United States Patent [19]

Leiner

[11] Patent Number: 4,969,708

[45] Date of Patent: Nov. 13, 1990

[54] FIBEROPTIC ENDOSCOPE

[76] Inventor: Dennis C. Leiner, 226 River St., Jaffrey, N.H. 03452

[21] Appl. No.: 385,387

[22] Filed: Jul. 27, 1989

[51] Int. Cl.⁵ .............................................. G02B 23/26
[52] U.S. Cl. ............................... 350/96.25; 350/96.26; 128/4
[58] Field of Search ............. 350/573, 569, 286, 96.1, 350/96.15, 96.19, 96.24, 96.25, 96.26; 128/4-8

[56] References Cited

U.S. PATENT DOCUMENTS

| | | | |
|---|---|---|---|
| 3,901,220 | 8/1975 | Koyasu et al. | 350/96.26 |
| 4,111,529 | 9/1978 | Yamashita | 128/6 |
| 4,158,475 | 6/1979 | Dianetti et al. | 350/573 |
| 4,704,000 | 11/1987 | Pekar et al. | 350/569 |
| 4,723,842 | 2/1988 | Twisselmann et al. | 350/569 |
| 4,735,473 | 4/1988 | Migozzi et al. | 350/96.25 |
| 4,754,470 | 5/1988 | Yabe et al. | 128/6 |
| 4,850,342 | 7/1989 | Hashiguchi et al. | 128/6 |

Primary Examiner—John D. Lee
Assistant Examiner—John Ngo

[57] ABSTRACT

An optical system for an endoscope is disclosed as having a direction of view at an angle to its axis, and which transmits in full color contrast two-dimensional optical images from an object plane to a final image plane. The optical system comprises a first light relaying system, a fiber optic assembly and a second light relaying system. The first light relaying system includes objective lenses positioned to focus light rays from an object at the entrance of the fiber optic assembly. The first light relaying means also includes a prism for dispersing the light from the object and for providing a direction of view at an angle of 30 to 60 degrees with respect to the axis of the system. The second light relaying system comprises lenses which are focused upon the exit end of the fiber optical assembly and are arranged to form an image of light rays transmitted thereby at a final image plane. The second relay system also includes light dispersing means so disposed relative to the exit end of the assembly as to disperse the light rays received from each assembly to recombine them.

3 Claims, 1 Drawing Sheet

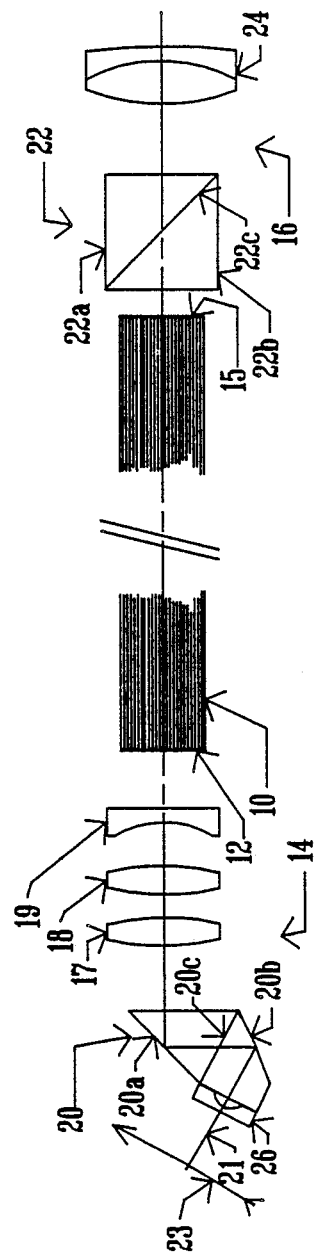

FIBEROPTIC ENDOSCOPE

BACKGROUND OF THE INVENTION

This invention relates generally to endoscopes for use in viewing a region within a body cavity. Endoscopes are optical instruments which are well known in the art, and are very useful in permitting the examination of body cavities without the need for extensive surgery. Currently used endoscopes are comprised of many optical lenses mounted in a tube to relay an image from inside a body cavity for viewing by a physician in order to diagnose various diseases or conditions.

A well known optical system currently in use is disclosed and claimed in U.S. Pat. No. 3,449,037 issued to C. J. Koester on June 10, 1969. The Koester patent discloses a two-dimensional optical image transmitting system which employs a fiber optic bundle, or an equivalent assembly, which is disposed in the optical system so as to have its entrance end portion arranged in optical alignment with a first light relaying system and its exit end portion arranged in optical alignment with a similar light relaying system. The fiber optical system was preferably square in cross section. The first relay system included a prism for providing chromatic dispersion for dispersing the various colors of the white light in a linear array. The second relay system included a second chromatic dispersion prism for recombining the dispersed light.

As Koester pointed out in his patent, prior fiber optical system had experienced difficulty in obtaining high quality resolution in the transmitted image due partly to the appearance of dark spots within the transmitted images caused by reduced transmittance or discontinuity in one or more of the elemental image transmission channels of the fiberoptic bundle, and also partly because of the grid-like or chicken wire effect which appeared in the transmitted image because of the spaces between the individual channels. Koester's use of the chromatic dispersion prisms overcame much of those deficiencies.

For an endoscope, the requirement for an overall diameter of the portion that is inserted into the body is severe, the maximum being of the order of 4 mm. Since room must be allocated for fiberoptic illumination and various mounting tubes, the dimeter of the optical elements is on the order of 2.5 mm. In addition, a further requirement of endoscopes is to have the direction of the field of view inclined at an angle of 30 to 60 degrees or more. In order to achieve the required field of view of between 80 and 100 degrees with maximum brightness, the endoscope objective uses what is known as a "retrofocus" optical design. This design makes it difficult to place both the Koester dispersing prism and the required direction of view prism between the distal negative lens component and the positive lens component while still transmitting a bright and wide field of view. This invention is an improvement over the prior art in that I use a single prism which is a combination of the Koester dispersing prism and the conventional direction of view prism, thereby accomplishing the results of both prisms within extraordinarily small dimensions required for the proper use of an endoscope.

OBJECTS OF THE INVENTION

It is a primary object of my invention to combine the action of a direction of view prism with the action of a dispersing prism. Another object of this invention is to use a prism in the objective lens system of an endoscope which has the combined characteristic of a direction of view prism and a dispersing prism so as to minimize the glass path in the objective lens system, thereby permitting maximum brightness and field of view.

Still another object of this invention is to combine the action of a direction of view prism with the action of a dispersing prism, by using a prism constructed of two different types of glass or plastic which will have similar refractive indices but difference dispersion characteristics.

SUMMARY OF THE INVENTION

In summary, this invention provide an optical system having a direction of view at an angle to its axis, and which transmits in full color two-dimensional optical images from an object plane to a final image plane. The optical system comprises a first light relaying system, a fiber optic assembly and a second light relaying system. The fiber optic assembly comprises a large number of thin elongated light conducting components having their respective opposite end portions arranged in adjacent side by side parallel relation to one another in like geometric arrays so as to provide similar bundle-like formations at its opposite planar optically finished ends. The first light relaying system comprises means to focus light rays from an object at said object plane substantially at the entrance of said fiber optic assembly. The first light relaying means also includes a prism for dispersing the light from the object and for providing a direction of view at an angle of 30 to 60 degrees or more with respect to the axis of the system. The light dispersing means is positioned in such fixed spaced relation to said entrance end of the fiber optical assembly as to disperse the component wavelengths of said light rays from each different object point into a spectrum of colors in a transverse direction at the entrance end of the fiber optics so that each spectrum is of such size as to have the component wavelength thereof impinge upon at least several adjacent light conducting components. The second light relaying system comprises lenses which are focused upon the exit end of the fiber optical assembly and are arranged to form an image of light rays transmitted thereby at a final image plane. The second relay system also includes light dispersing means so disposed in fixed spaced relation relative to the exit end of said assembly and so oriented relative thereto as to disperse the light rays received from such assembly in such a manner as to recombine all the component wavelengths and form an image in full color contrast at the final image plane.

BRIEF DESCRIPTION OF THE DRAWING

For further objects and advantages of this invention, reference should now be made to the following specification and drawing in which:

the single FIGURE is a schematic representation of a preferred embodiment of the invention.

DESCRIPTION OF THE DISCLOSED EMBODIMENT

Referring to single figure of the drawing, the endoscope system is illustrated as comprising a fiber optical bundle indicated generally by the numeral 10 and disposed so that it optically polished entrance end portion 12 is arranged in optical alignment with a first light relaying system 14, and so that its optically polished exit end portion 15 is arranged in optical alignment with a similar light relaying system 16.

The fiber optic bundle 10 is similar to that used in the aforesaid Koester patent, and as in Koester has all of the fiber optic elements maintained in a parallel orientation so that the image appearing on the entrance end portion 12 is the same as the image at the exit end portion 15. The fiber optic assembly comprises a large number of thin elongated light conducting components having their respective opposite end portions arranged in adjacent side by side parallel relation to one another in like geometric arrays so as to provide similar bundle-like formations at its opposite planar optically finished ends.

The objective lens system 14 comprises first, second and third lenses 17, 18 and 19 having positive power when used in combination and a negative field widening lens 26, all aligned along the optical axis of the system. Also included in the objective lens system 14 is a prism 20, which involves the essence of this invention.

The prism 20 is formed of two portions 20a and 20b fixed together at 20c. The prism 20 serves to disperse the white light rays in exactly the manner taught by Koester in U.S. Pat. No. 3,449,037; however, the two portions of the Prism 20a and 20b also serve in combination to change the direction of view of the system to an angle of 30 to 60 degrees or more off the optical axis, whereby an object in the object plane any be viewed at angle to the mechanical axis.

The prism 20 is made of two different types of glass such as LaSFN30 for prism portion 20b and SF6 for prism portion 20a. These types of glass or plastic have similar refractive indices, but different dispersions. Depending on the desired dispersion in the system, the angle at which the two parts of the prism are joined can be altered. It will be noted that the rays 21 from an object being viewed in the object plane 23 are reflected twice, so as to maintain the image in its original reversion. By using the prism for both dispersion and change of view, the need for a second prism system is eliminated, and the severe space requirements of the endoscope are achieved.

The dispersed light rays 21 pass through the fiberoptic bundle 10 and pass through the dispersion prism 22 and the ocular lens 24. The prism 22 is comprised of two portions 22a and 22b fixed together at 22c, and seves to recombine the dispersed light for viewing through ocular lens 23. The prism portions of prism 22 are made of the same two materials as the portions of prism 16. However, prism 22 is not provided with the reflective paths of prism 16, so that the rays continue on the axis of the system.

It will be seen there is provided an optical system which has a direction of view at an angle to its axis, and which treansmits light from an object plane to a final image plane. The include a fiber optic assembly on to which dispersed light is focused at one end and recombined as the light exits the other end. Object light relaying system means include a prism for dispersing the light from the object and for providing a direction of view at an angle of 30 to 60 degrees or more with respect to the axis of the system.

While only a single embodiment of this invention has been described, it will be apparent to persons skilled in the art that the invention is subject to many variations and adaptations within the spirit and scope of this invention. For example, various configurations of prisms may be used, provided that an even number of reflective paths are used in the complete system. The prism may be made of glass, as used in the example, or it may be made of plastic, so long as the characteristics are as set forth. Moreover, the fiber optic bundle may be of any reasonable length so long as the entrance end presents the same geometrical array as the exit end. It is intended therefore, that this invention be limited only by the appended claims as interpreted in the light of the prior art.

I claim:

1. An optical system for transmitting optical images from an object plane to a final image plane, said optical system haivng a mechanical axis, said system focussing light on an image plane, the object plane of said system being at an angle with respect to said axis, said optical system comprising a first light relaying system, a fiber optic assembly, and a second light relaying system all being disposed in optical alignment, the fiber optic assembly being configured so as to provide identical formations at its opposite optically polished planar entrance and exit ends, said first light relaying system comprising means positioned to focus light rays from said object plane on the entrance end of said fiber optical assembly and also comprising first light dispersing means, said first light dispersing means being position in such fixed space relation to said entrance end as to disperse the component wavelengths of said light rays from each different object point into a spectrum of colors in a transverse direction at said entrance end and with each spectrum of such size as to have the component wavelenghts thereof impinge upon at least several adjacent light conducting components, said first light dispersing means comprising a first prism constructed of first and second prism portions said portions being fixed together, the surfaces of said portions dispersing said light and directing said light to said entrance end through two reflection paths, said portions having similar refractive characteristics and dissimilar dispersion characteristics, said second light relaying system comprising lens means focussed upon the exit end of said fiber optical assembly and arranged to form an image of light rays transmitted thereby at said final image plane and light dispersing means so disposed in fixed spaced relation relative to the exit end of said assembly and so oriented relative thereto as to disperse the light rays received from such assembly in such a manner as to recombine said component wavelengths and form an image in full color contrast at said final image plane.

2. The invention as defined in claim 1 wherein said prism is comprised of first and second prism portions, said portions being made of glass having similar refractive characteristics and dissimilar dispersion characteristics, said portions in combination providing two reflection paths for said light.

3. The invention as defined in claim 1 wherein said prism is comprised of first and second prism portions, said portions being made of plastic having similar refractive characteristics and dissimilar dispersion characteristics, said portions in combination providing two reflection paths for said light.

* * * * *